(12) United States Patent
Subbhuraam et al.

(10) Patent No.: US 11,672,427 B2
(45) Date of Patent: Jun. 13, 2023

(54) SYSTEMS AND METHODS FOR TISSUE ASSESSMENT

(71) Applicant: CYRCADIA ASIA, LTD., Wanchai (HK)

(72) Inventors: Vinitha Sree Subbhuraam, Houston, TX (US); Robert James Royea, Hong Kong (HK)

(73) Assignee: CYRCADIA ASIA, LTD., Wanchai (HK)

( * ) Notice: Subject to any disclaimer, the term of this patent is extended or adjusted under 35 U.S.C. 154(b) by 193 days.

(21) Appl. No.: 16/528,411

(22) Filed: Jul. 31, 2019

(65) Prior Publication Data

US 2020/0037885 A1 Feb. 6, 2020

Related U.S. Application Data

(60) Provisional application No. 62/714,033, filed on Aug. 2, 2018.

(51) Int. Cl.
*A61B 5/01* (2006.01)
*G16H 50/50* (2018.01)
(Continued)

(52) U.S. Cl.
CPC ............... *A61B 5/01* (2013.01); *A61B 5/002* (2013.01); *A61B 5/0008* (2013.01); *A61B 5/015* (2013.01);
(Continued)

(58) Field of Classification Search
CPC ....... A61B 5/0008; A61B 5/0091; A61B 5/01; A61B 5/015; A61B 5/4312; A61B 5/4857; A61B 5/6805; A61B 5/6823; A61B 5/7264; A61B 5/7275; A61B 2562/0271; A61B 5/002; A61B 5/7267; G16H 50/20;
(Continued)

(56) References Cited

U.S. PATENT DOCUMENTS 3,960,138 A * 6/1976 Doss ................... A61B 5/01
600/549
5,941,832 A 8/1999 Tumey
(Continued)

FOREIGN PATENT DOCUMENTS

| CN | 104687276 A | 6/2015 | |
|---|---|---|---|
| JP | 2019511707 A | 4/2019 | |
| WO | WO-2012143721 A1 * | 10/2012 | ........... A61B 5/6804 |

OTHER PUBLICATIONS

"XGBoost Documentation", 2021, xgboost developers (Year: 2021).*
(Continued)

*Primary Examiner* — Patrick Fernandes
*Assistant Examiner* — Anna Roberts
(74) *Attorney, Agent, or Firm* — Zhong Law, LLC

(57) ABSTRACT

Systems, methods, and computer program products are disclosed that can receive temperature data from at least one temperature sensor over a period of time. At least one metric of the temperature data can be calculated, which may utilize the temperature data from a particular sensor over the period of time and may be indicative of variability in the temperature data. A tissue assessment can be determined by utilizing a classifier with at least one feature input to the classifier, the feature(s) being determined from the metric(s).

15 Claims, 11 Drawing Sheets

(51) Int. Cl.
*G16H 50/20* (2018.01)
*A61B 5/00* (2006.01)
*G06N 3/08* (2023.01)
*G01K 13/20* (2021.01)
*G16H 50/30* (2018.01)

(52) U.S. Cl.
CPC .......... *A61B 5/4312* (2013.01); *A61B 5/4857* (2013.01); *A61B 5/6823* (2013.01); *A61B 5/7264* (2013.01); *A61B 5/7275* (2013.01); *G01K 13/20* (2021.01); *G06N 3/08* (2013.01); *G16H 50/20* (2018.01); *G16H 50/50* (2018.01); *A61B 5/0091* (2013.01); *G16H 50/30* (2018.01)

(58) Field of Classification Search
CPC ........ G16H 50/30; G16H 50/50; G01K 13/20; G06N 3/08
See application file for complete search history.

(56) References Cited

U.S. PATENT DOCUMENTS 8,185,485 B2  5/2012  Keith
8,231,542 B2  7/2012  Keith
2010/0056945 A1* 3/2010  Holmes ................ A61B 5/7267
                                                              600/549
2017/0242234 A1  8/2017  Ashcroft et al.
2019/0106732 A1* 4/2019  Spurlock, III ....... C12Q 1/6883

OTHER PUBLICATIONS

"XGBoost Classifier" Mar. 6, 2021, apmonitor.com (Year: 2021).*
Farrar, W. B., et al., "An Evaluation of a New Objective Method for Early Breast Cancer Screening," Study, The Ohio State University College of Medicine, Columbus, OH, 4 pages.
Keith, L. G., et al., "Circadian Rhythm Chaos: A New Breast Cancer Marker," Int. J. Fertil. Womens Med., Sep.-Oct. 2001; 46(5): 238-247.
International Search Report and Written Opinion, International Application No. PCT/IB2019/000881, International Filing Date Jul. 31, 2019.
Notice of Reasons for Refusal received in Japanese Application No. 2021-505897 dated Feb. 21, 2023, pp. 1-7.
Search Report received in Japanese Application No. 2021-505897 dated Feb. 15, 2023, pp. 1-58.

* cited by examiner

SYSTEMS AND METHODS FOR TISSUE ASSESSMENT

RELATED APPLICATION(S)

This application claims priority to and the benefit of U.S. Provisional Application No. 62/714,033, filed Aug. 2, 2018, titled "Systems And Methods For Analyzing Skin Surface Temperature Rhythms To Monitor Health Conditions," which is hereby incorporated by reference.

DESCRIPTION OF THE RELATED ART

Breast cancer refers to the erratic growth and proliferation of cells that originate in breast tissue. The global impact of breast cancer is significant and continuously increasing. In most nations, the mortality rate from breast cancer is high primarily due to a lack of screening protocols, early detection technologies that are comfortable and radiation-free, and access to quality care. An affordable in-home breast health monitoring device that can efficiently diagnose the presence of early abnormal breast tissue changes without the need for trained professionals has the potential to significantly improve survival rates.

SUMMARY

Systems, methods, computer program products (software), and devices are disclosed for acquiring temperature data that may optionally be used to create a tissue assessment. One such system includes a processor and software that perform various operations, including receiving temperature data from at least one temperature sensor over a period of time. The operations also include calculating at least one metric of the temperature data, the metric(s) utilizing the temperature data from a particular sensor over the period of time and being indicative of variability in the temperature data. Then, a tissue assessment is determined by utilizing a classifier with at least one feature input to the classifier, the feature(s) determined from the metric(s).

In some implementations, the temperature data can be received from multiple temperature sensors, where multiple metrics are calculated from the temperature data, and where multiple features are input to the classifier. The determined tissue assessment can be normal, benign, or malignant.

In other implementations, the system can include a wearable device, such as a bra, with temperature sensors integrated into the wearable device to measure the temperature data particular locations on a breast.

In yet other implementations, the features can be determined utilizing a metric from multiple temperature sensors. Also, the features can utilize the temperature data from one side of a body and temperature data from a corresponding location on the opposite side of the body.

In some implementations, the period of time (for the temperature data) can be approximately twenty-four hours. For such a period of time, the metric(s) can include a Mean, a Largest Lyapunov Exponent, and a Short Hurst Exponent, with the features optionally including a Mean1, a LLE7, and a SHE12, and the classifier optionally being an SVM classifier with a Radial Basis Function kernel.

In other implementations, the period of time can be approximately two hours. For this period of time, the metric(s) can include a SensorDiff and an ApEn, with the features optionally including a SensorDiff3, an ApEn3, and an ApEn5, and the classifier optionally being an XGBoost classifier.

Also disclosed is a system for analyzing temperature changes in breast tissue to determine a suspect condition. The system can include a pair of patches having temperature sensors on each patch, a recorder to record temperature from each of the temperature sensors over a period of time, and a transmission device for communicating the recorded temperatures to a computing device for determining a breast tissue classification.

In some implementations there can be eight temperature sensors on each patch, and the temperature sensors can be placed on locations predominantly associated with breast cancer. The period of time can be two hours and the transmission device can communicate recorded temperatures to the computing device via Bluetooth™.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Various aspects of the present disclosure describe devices, systems, software, and methods that can, among other things, utilize predictive analyses of skin surface temperature rhythms for assessing and/or monitoring breast tissue. People exhibit certain biological rhythms (e.g., circadian rhythms) in, for example, body temperatures. As further explained herein, cancerous and noncancerous tissue can exhibit different temperature behaviors. By training a predictive model to interpret certain temperature related data from patient tissues, a predictive model can provide an assessment of whether a given set of temperature data is normal or abnormal.

Figure 1:
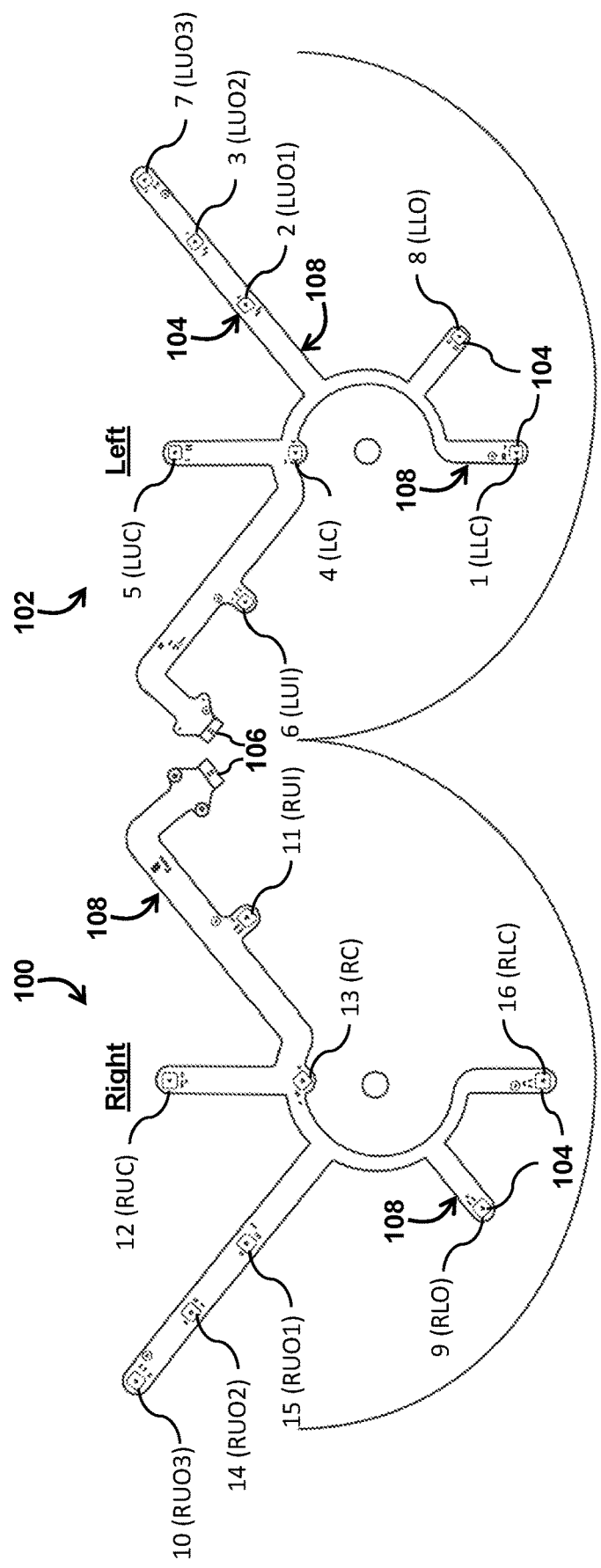
FIG. 1 is a simplified diagram illustrating an exemplary wearable device showing the relative positioning of thermal sensors on the left and right breasts of a patient in accordance with certain aspects of the present disclosure.

To assess breast tissue, one or more temperature sensors can be utilized to measure temperatures at the surface of a breast. FIG. 1 depicts one example of a wearable device with one or more (in this example several) temperature sensors 104 integrated into the wearable device. The wearable device can have of a pair of wearable, non-invasive, comfortable and reusable self-adhering breast patches 100 and 102. In various implementations, the wearable device can be worn under (or incorporated into) a bra to capture temperature changes within breast tissue. In some implementations, each patch can include one or more arms 108 for locating and supporting sensors proximate to desired measurement locations. As shown, the arms can be generally radial and allow sensors to be located at particular locations on the breast. In other implementations, different supporting frameworks can be used to position the temperature sensors. The temperature sensors can be wired to connectors 106, which may then be connected to a recorder that collects the captured temperature data. The recorder may contain a battery to power the patches, a memory, and a low-energy Bluetooth™ transmission device, which can communicate the recorded data to an external computing device.

The arrangement of the temperature sensors can be configured to measure temperature data at one or more particular locations on a breast. In the exemplary implementation shown in FIG. 1, temperature sensors 104 are labeled 1-16 to denote specific sensors, as well as including abbreviations that generally describe their location (e.g., Right Upper Outer at position #3 (RUO3), Left Center (LC), etc.). In FIG. 1, the exemplary temperature sensor marked 1 corresponds to a temperature sensor located at approximately the lower center location of the left breast. Similarly, temperature sensor 11 corresponds to the upper inner portion of the right breast. While the present disclosure illustrates temperature sensors at particular locations on the breast and having an exemplary numbering and layout, other locations, numberings, and layouts are contemplated.

In an exemplary embodiment, the wearable device can record temperature data from each of the sensors over a period of two hours. In other embodiments, the wearable device may record temperature data over different periods of time, approximately 2 hours, approximately 2 to 6 hours, approximately 24 hours, or up to approximately 48 hours. In some implementations, shorter acquisition times may be desired to improve patient adoption. Shorter acquisition times may also be less susceptible to environmental interference and other fluctuations.

As used herein, "temperature data" can refer to a relatively large set of temperature data acquired over a lengthy span of time from a large number of sensors via analog acquisition or a high sampling rate. However, "temperature data" can also refer to a smaller set of temperature data, for example, a dataset that includes temperature data from just four sensors over a two-hour timespan.

In some implementations, temperature sensor locations on the left breast patch may be a mirror image of the sensor locations on the right breast patch. The patches' sensor locations can have a specific spatial alignment that may be based upon the predominance of breast cancer locations within a woman's breast.

To ensure that the wearable device can be used with various breast sizes, the patches may be available in different sizes. The patient can select a patch of appropriate size (e.g., #1-#15) based upon the traditional bra cup and chest size as shown in the following sizing charts of Table 1.

TABLE 1

| Cup Size | Bra Size | | | | | | | | |
|---|---|---|---|---|---|---|---|---|---|
| | 32 | 34 | 36 | 38 | 40 | 42 | 44 | 46 | 48 |
| A− | — | 2 | 4 | 5 | 7 | 9 | 11 | — | — |
| A+ | 1 | 3 | 5 | 6 | 8 | 10 | 12 | — | — |
| B− | 2 | 5 | 6 | 7 | 9 | 11 | 12 | 13 | 14 |
| B+ | 3 | 6 | 7 | 8 | 10 | 12 | 13 | — | — |
| C− | 4 | 7 | 8 | 10 | 11 | 12 | 13 | 14 | 15 |
| C+ | 5 | 8 | 9 | 11 | 12 | 13 | 14 | — | — |
| D− | 6 | 9 | 11 | 13 | 13 | 14 | — | — | — |
| D+ | 7 | 10 | 12 | — | — | — | — | — | — |

| | Length (at widest) | Width (at thickest part) |
|---|---|---|
| 1 | 5¾" | 4" |
| 2 | 6" | 4¼" |
| 3 | 6¼" | 4½" |
| 4 | 6½" | 4¾" |
| 5 | 6¾" | 5" |
| 6 | 7" | 5⅛" |
| 7 | 7¼" | 5⅛" |
| 8 | 7¼" | 5½" |
| 9 | 7½" | 5½" |
| 10 | 7¾" | 5¾" |
| 11 | 8" | 5¾" |
| 12 | 8" | 6" |
| 13 | 8¼" | 6½" |
| 14 | 8½" | 6½" |
| 15 | 8¾" | 6¾" |

Figure 2A:
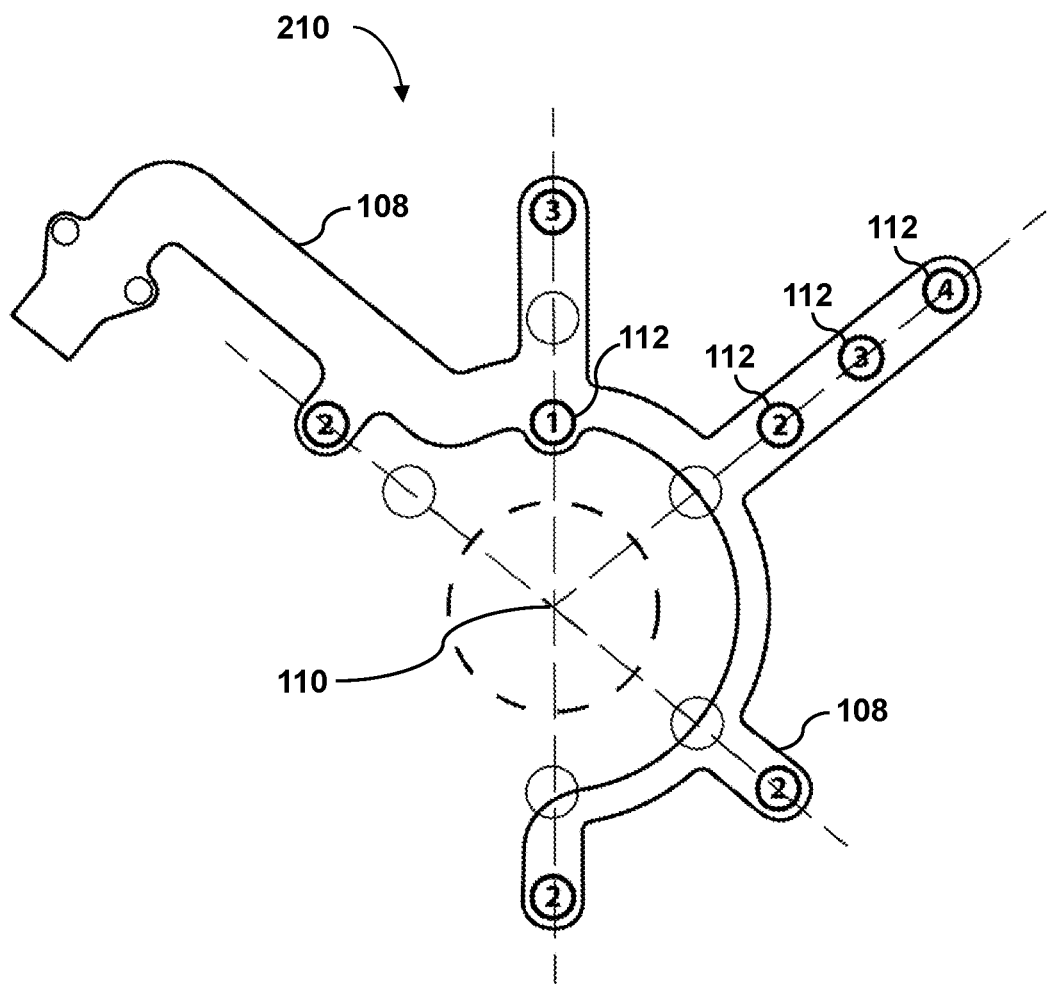
FIGS. 2A and 2B are simplified diagrams illustrating exemplary patch sizes for the wearable device, including examples of the placement of temperature sensors on each patch in accordance with certain aspects of the present disclosure.
Figure 2B:
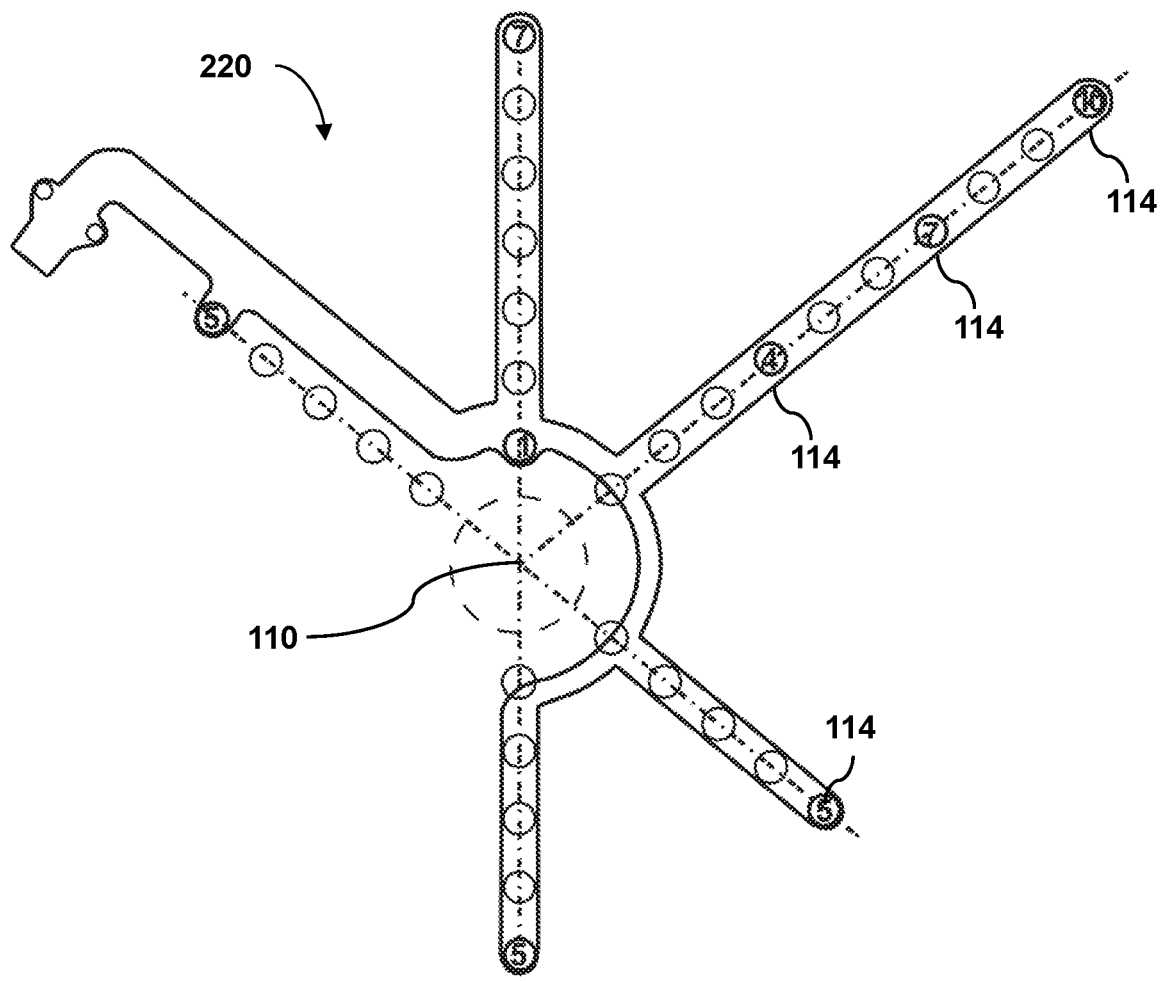

FIGS. 2A and 2B illustrate two embodiments (210, 220) of the different patch sizes #3 and #13 of Table 1—and the approximate sensor placements on each patch size. The arms 108 are shown extending generally radially from a central point. An arm may include one or more holes 112 (or other temperature sensor coupling features, such as pockets, being sewn into the patch, embedded in the patch material, etc.) in which a temperature sensor may be placed. The holes can be labeled based on an approximate distance from a central point 110 of the patch. For example, in FIG. 2A, hole 112 distances 1, 2, 3, and 4 are respectively approximately 22 mm, 34.7 mm, 47.4 mm, and 60.1 mm. In FIG. 2B, holes 114 distances 4, 5, 7, and 10 are respectively approximately 60.1 mm, 72.8 mm, 98.2 mm, and 136.3 mm. Although arm length can vary depending on the patch size, the hole distances may remain consistent throughout the various patch sizes (e.g., hole 1 can be approximately 22 mm from the center in both FIGS. 2A and 2B). As noted above, the temperature sensor placement for each patch 100 and 102 can be based on patch size and desired locations based on, for example, the predominant locations of breast cancer. Accordingly, the placement of the temperature sensors from a central point 100 can change such that approximate sensor location relative to the breast is consistent regardless of patch size or design.

Figure 3A:
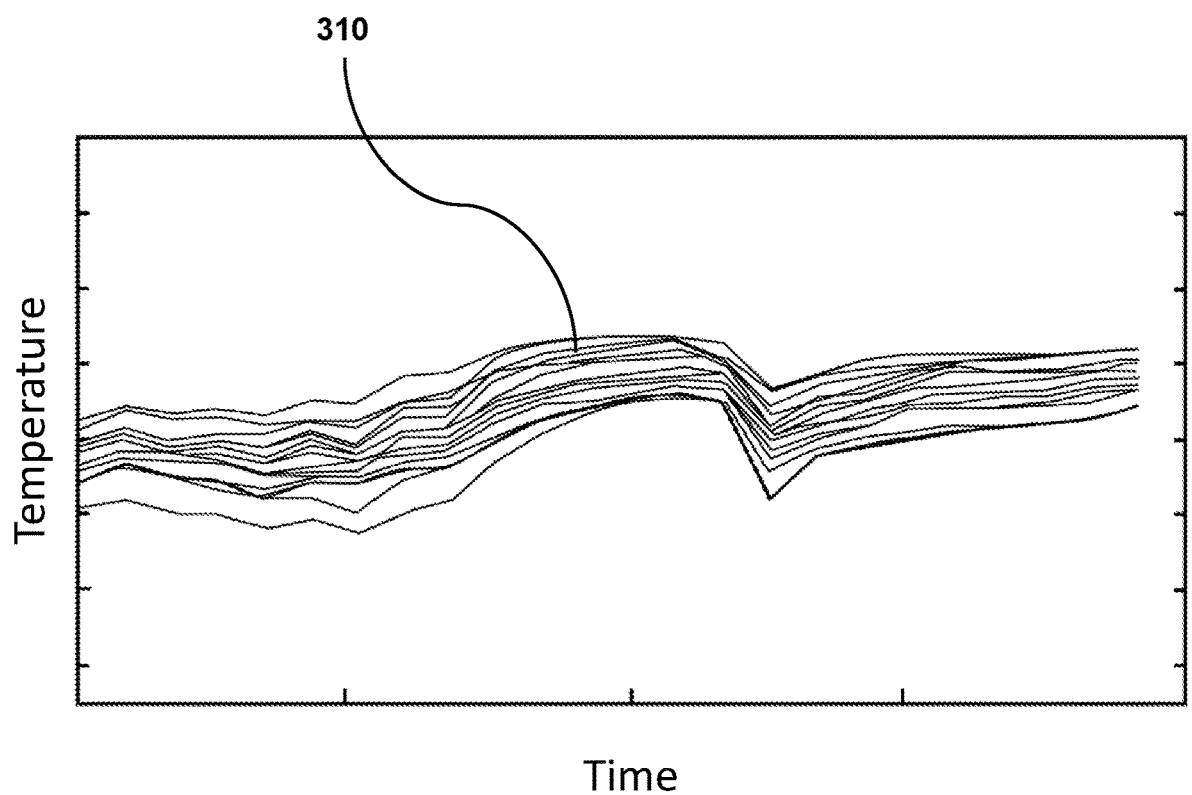
FIGS. 3A and 3B are simplified diagrams illustrating examples of temperature readings over time with regard to a benign lesion in accordance with certain aspects of the present disclosure.
Figure 3B:
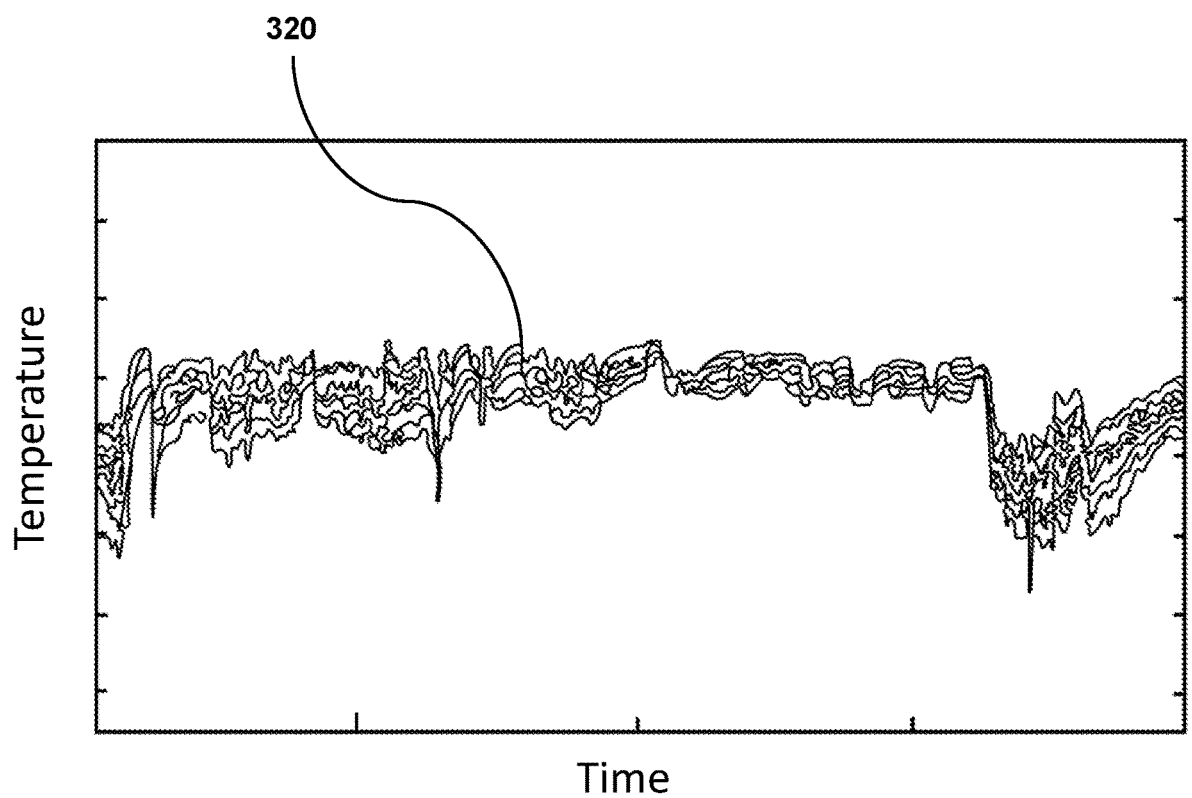
Figure 4A:
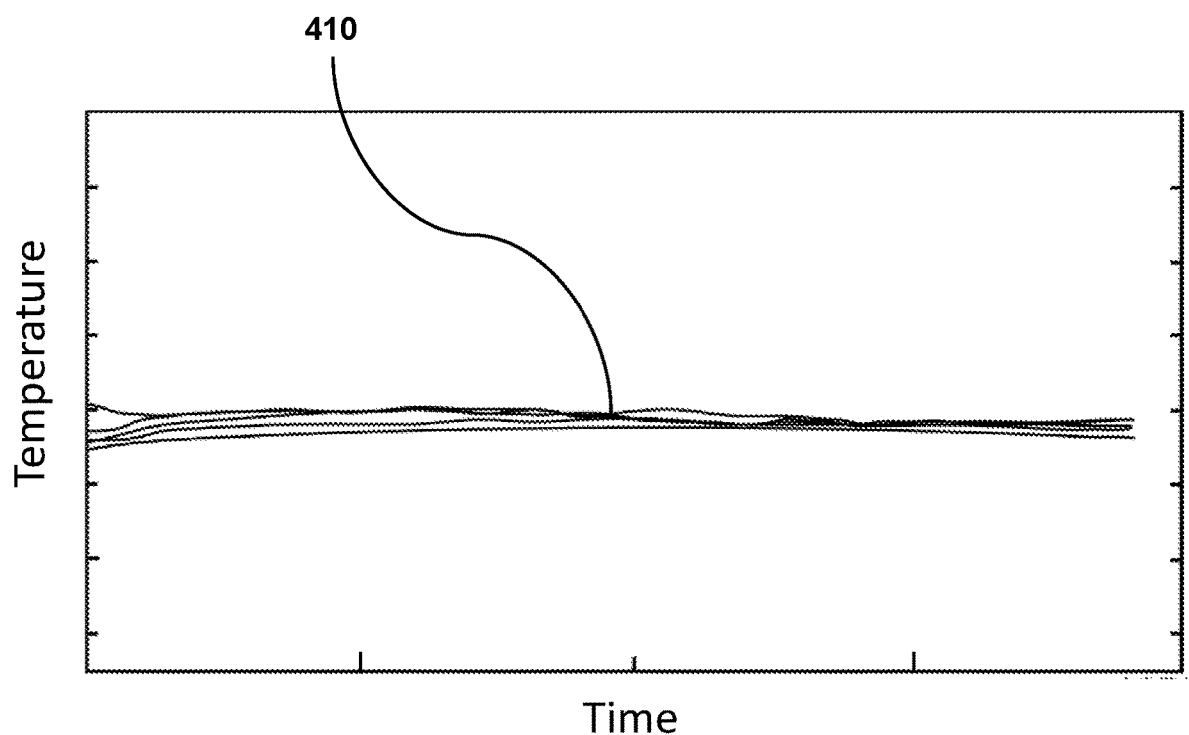
FIGS. 4A and 4B are simplified diagrams illustrating examples of temperature readings over time with regard to a malignant lesion in accordance with certain aspects of the present disclosure.
Figure 4B:
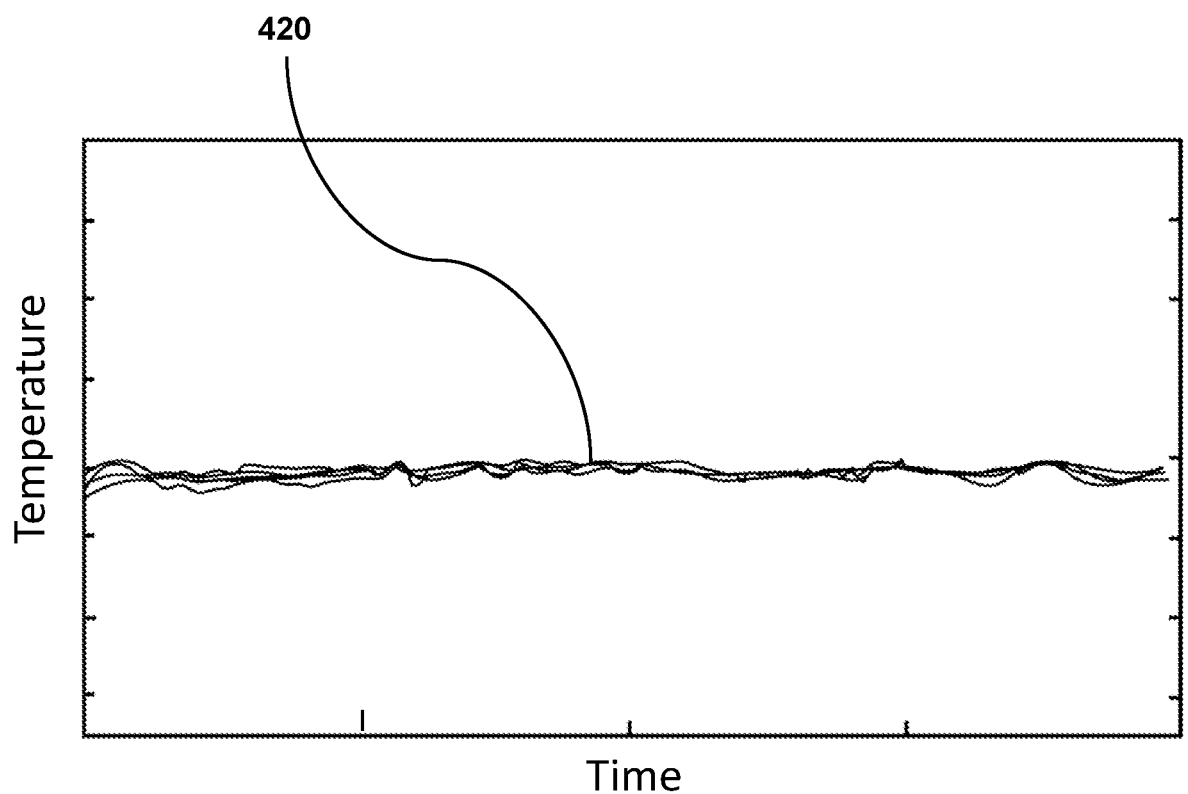

Recorded temperature data from the wearable device can form a multidimensional time series dataset, such as temperature values from the available temperature sensors over a given time period. FIGS. 3A and 3B illustrate examples of temperature data 310, 320 from several temperature sensors over a time period of 2 and 24 hours, respectively, from breast tissue having a benign lesion. The examples show that the temperature data from each of the sensors generally follows the same circadian rhythm. FIGS. 4A and 4B illustrate temperature data 410, 420 over similar time periods of 2 and 24 hours, respectively, but where the breast tissue includes a malignant lesion. In benign or malignant tissue abnormalities, clear segments of time-phase metabolic change and thermo-circadian rhythm variation can be visualized as periods of temperature data compression (amplitude and period) and differential (relative minima and maxima of sensors temperature).

As illustrated, temperature variations for a patient having a benign lesion (FIGS. 3A and 3B) over the measured time period are greater than the variations in malignant lesion measurements (FIGS. 4A and 4B) over a similar time period. In general, higher variations are seen in the thermal profile obtained from non-cancerous tissue. This is due, in part, because the superficial thermal pattern of the breast is related to metabolism and vascularization within the underlying tissues, thus resulting in significant temperature changes, not just in amplitude, but also in variability over time.

Figure 5:
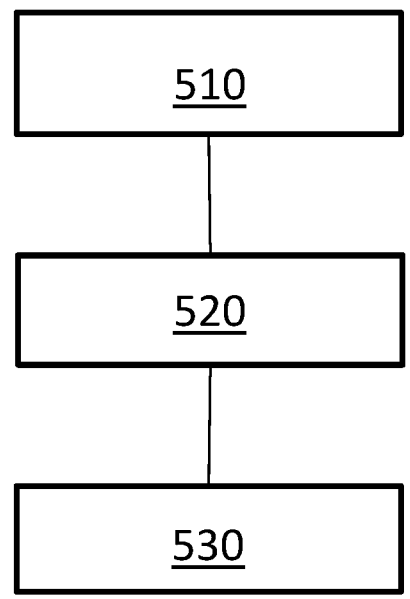
FIG. 5 is a simplified diagram illustrating exemplary operations for patient tissue assessment in accordance with certain aspects of the present disclosure.

As discussed below, with further reference to FIGS. 5 and 6, some implementations of the present disclosure can utilize temperature information with one or more predictive models to analyze observed temperature fluctuations and generate an assessment of breast tissue from which skin surface temperatures have been recorded. In various implementations, a predictive model can base an assessment on temporal variations (or reduction of such) in temperature that occur at the early stages of tumor growth. For example, the assessment can include determining a tissue classification, such as cancerous or not cancerous, "normal" (e.g., no lesions), "benign" (e.g., not harmful), or "malignant" (e.g., cancerous).

One exemplary system for tissue assessment can include a processor and software that can perform various operations for assessing tissue. As illustrated in FIG. 5, the operations can include, at 510, receiving temperature data from at least one temperature sensor over a period of time (e.g., approximately 2 hours or 24 hours). At 520, metric(s) (e.g., a variance) of the temperature data can be calculated utilizing the temperature data from a particular sensor over the period of time, which metrics are indicative of variability in the temperature data. At 530, a tissue assessment can be determined by utilizing a classifier (e.g., a neural network trained to make an assessment) with at least one feature input to the classifier. The "features" can be determined from the metrics, as described further herein.

In certain embodiments contemplated herein, the temperature data can be received from multiple temperature sensors, multiple metrics can be calculated from the temperature data, and multiple features can be input to the classifier.

As used herein, the term "variability" relates to changes (e.g., in temperature) over time. For example, a collection of temperature data may have a greater variability if its variance is larger. In another example, variability can be related to a degree of chaos or randomness derived from the data. Other measures of variability are described herein.

The present disclosure describes methods for determining and utilizing aspects of variability in temperature data to make a tissue assessment. However, it is contemplated that quantities other than variability (e.g., the temperature values themselves, their means or averages, etc.) may optionally be incorporated into the assessment. Also, while reference is made herein to methods that analyze temperature data, the disclosed methods can also be applied to other types of physiological or sensed data and the variability of such data can be similarly analyzed as part of making an assessment of a health condition.

Tissue assessment may be generated by a predictive model that has been trained to accurately assess tissue based on available data. As explained in further detail below, a "predictive model," as used herein, is a combination of a "classifier" (e.g., a particular type of neural network or other classification algorithm) and one or more "features" (e.g., a combination of one or more metric(s), such as a variance, from one or more particular sensor(s), such as sensor 3). The classifier can be trained with training data (having a known assessment) and testing data (to test the accuracy of the predictive model on unassessed data). In some implementations, as illustrated in FIG. 6, the process of developing and deploying a predictive model can include: Data Acquisition 610, Data Preprocessing 620, Metric Calculation 630, Feature Determination 640, Feature Subset Selection 650, Predictive Model Development and Evaluation 660, and Predictive Model Deployment 670.

Data acquisition 610 can include obtaining temperature data from one or more temperature sensors on a wearable device. A data recorder associated with the wearable device may have software to scan temperature sensors at predetermined time intervals (e.g., every 10 seconds or 60 seconds), and to store sensed temperature data until the chosen measurement cycle time, (e.g., two hours), elapses.

Data preprocessing 620 can be used to improve the quality of the temperature data by, for example, removing incomplete data or outliers. For example, if temperature data at a given time has missing data, that entry (e.g., data from all sensors at that time) can be removed. An entry can also be removed when there is a value outside a particular threshold (e.g., perhaps where a sensor was not contacting the patient properly). The threshold can be, for example, defined as any temperature record (e.g., a set of 16 sensor values) with values<27 C. Thus, any entry having a value below the threshold can be removed. Alternatively, if there are more than a given number of bad entries (e.g., three), the temperature data from the patient can be rejected for analysis entirely.

Metric calculation 630 can include using, for example, the preprocessed temperature data over time to calculate metrics that may capture variability in the temperature data. For example, in some implementations, metric(s) can be calculated from temperature data such as: Mean, Variance (Var), Approximate Entropy (ApEn), Fractal Dimension (FD), Second Order Moment (Cum_2), Short Hurst Exponent (SHE), Largest Lyapunov Exponent (LLE), Mobility (Mob), Wavelet Entropy (WEnt), and Permutation Entropy (PE). Metrics other than those listed are also contemplated. These metrics may be calculated as described below, though it is understood that the exact details of the calculations of these metrics, including the particular nomenclature, steps, and order of calculation can have variations which may result in quantitatively or qualitatively similar metrics.

Mean: The mean $\mu$ is the average value of the time series A. It is calculated as follows (N is the number of observations):

$$\text{Mean} = \frac{1}{N}\sum_{i=1}^{N} A_i.$$

Variance (Var): The variance is a representation of the power of how far the time series fluctuates from its mean. The variance is defined as:

$$\text{Var} = \frac{1}{N-1}\sum_{i=1}^{N} \lceil A_i - \mu \rceil^2.$$

Approximate Entropy (ApEn): Approximate Entropy is a measure of complexity, and quantifies the unpredictability of fluctuations in a time series. ApEn is scale invariant and assigns a nonnegative number to a time series, with larger values corresponding to more irregularity in the data. Let the time series $A_N$ have N measurements TS(1), TS(2) . . . TS(N). To calculate approximate entropy $ApEn(A_N, m, r)$, two parameters are chosen first—m, which specifies the pattern length, and r defines the criterion of similarity. Let $p_m(t)$ denote a pattern of m measurements starting at measurement i within the series $A_N$. Two patterns $p_m(i)$ and Pm(j) are considered similar if the difference between any pair of corresponding measurements in both patterns is less than r. Let $P_m$ denote the set of all patterns of length m within $A_N$ beginning at measurements 1 to N−m+1. The correlation integral is defined by:

$$C_i^m(r) = \frac{n_{im}(r)}{N-m+1}.$$

Where $n_{im}(r)$ is the number of patterns similar to $p_m(t)$. The correlation integral is calculated for each pattern in $P_m$. Let $C_m(r)$ be the mean of all these $C_j^m(r)$ values. Approximate Entropy is defined as the natural logarithm of the relative occurrence of repetitive patterns of length m compared to repetitive patterns of length m+1 as below:

$$ApEn(A_N, m, r) = \ln\left[\frac{C_m(r)}{C_{m+1}(r)}\right]$$

Fractal Dimension (FD): FD is another measure of series complexity and the presence of transients in time series data. Let $\{a_i, a_2, a_3, a_N\}$ indicate a N dimensional time series. The first step is to form k new time series $A_k^m$ defined as follows:

$$A_k^m = \left\{a[m], a[m+k], a[m+2k], \ldots, a\left[m + int\left(\frac{N-m}{k}\right), k\right]\right\}$$

Where k indicates the discrete time interval between points, and m=1, 2, k represents the initial time value. The next step is to calculate the length of each new time series as follows:

$$L(m, k) = \frac{\left\{\left(\sum_{i=1}^{int\left(\frac{N-m}{k}\right)} a[m+ik] - a[m+(i-1)k]\right)\frac{N-1}{int\left(\frac{N-m}{k}\right)\cdot k}\right\}}{k}.$$

Mean value of the curve length L (k) is then calculated for each k by averaging L(m, k) for all m. FD is defined as the slope of the line that fits (least squares linear best fit) log(L(k)) and log $$\left(\frac{1}{k}\right).$$

Second Order Cumulant (Cum 2): Let (ax, a2, a3, aN} indicate a N dimensional time series. Its second order moment is defined as:

$$m_2^a(i) = E[a(n)a(n+i)]$$

E[ ] indicates the expectation operator. Using moments, the second order cumulant is calculated as:

$$\text{Cum}\_2_2^a = m_2^a(i)$$

Short Hurst Exponent (SHE): The Hurst exponent is a numerical estimate of the predictability of a time series. It is used to determine if the time series is more, less, or equally likely to increase if it has increased in previous steps. It is defined as:

$$SHE = \frac{\log\left(\frac{R}{S}\right)}{\log(T)}$$

T is the duration of the time series and RIS is the corresponding value of rescaled range. R is the difference between the maximum and minimum deviation from the mean and S is the standard deviation.

Largest Lyapunov Exponent (LLE): LLE is an indicator of chaos in the system. It defines the average rate by which two neighboring trajectories diverge or separate from one another. Consider two nearby points in a space as $x_0$ and $x_0 + \Delta x$ that are a function of time. Each of these points will generate an orbit of its own. The separation between the two orbits $\Delta x$ is a function of the location of the initial value and has the form $\Delta x(x_0, t)$. The mean exponential rate of divergence of these two orbits is measured as follows:

$$\lambda = \lim_{t \to \infty} \frac{1}{t} \ln \frac{|\Delta x(x_0, t)|}{|\Delta x|}.$$

LLE is the maximum positive value of $\lambda$. A positive LLE indicates the existence of chaos in that system.

Mobility (MOB): Mobility is the square root of variance of the first derivative of the data $A_N$ divided by the variance of the data $A_N$:

$$Mob = \sqrt{\frac{\text{Var}\left(\frac{dA}{dt}\right)}{\text{Var}(A)}}.$$

Wavelet Entropy (WEnt): Wavelet Entropy (WE) combines wavelet decomposition and entropy to estimate the degree of order/disorder of a signal with a high time-frequency resolution. Shannon entropy is commonly used to quantify the energy distribution in wavelet sub-bands and is also a measure of the spectral complexity of the time series. Let the power in each frequency in the time series be denoted by $p_f$. Wavelet entropy is calculated as the sum of the entropy over the entire frequency range as given by:

$$WEnt = \sum_f p_f \log\left[\frac{1}{p_f}\right]$$

Permutation Entropy (PE): Permutation entropy describes the complexity of a time series or signal and considers the randomness in the time series. It takes the temporal order of the measurements in the time series data into account and helps determine any couplings between time series. Large values indicate more randomness in the time series. Given a time series $A_N$, an embedding procedure is first used to form vectors with embedding dimension m and lag 1. For m different embedding dimensions, there will be m! possible permutations (order pattern) $\pi C$. Let $C(\pi_i)$ be the count of the occurrences of the order pattern $(\pi)_i$ where i=1, 2, . . . m! The relative frequency of $C(\pi_i)$ is given by $p(\pi)=C(\pi_i)/(N-(m-1)1$. The permutation entropy is defined as:

$$PE = \sum_{m=1}^{m!} p(\pi) \ln p(\pi).$$

Figure 6:
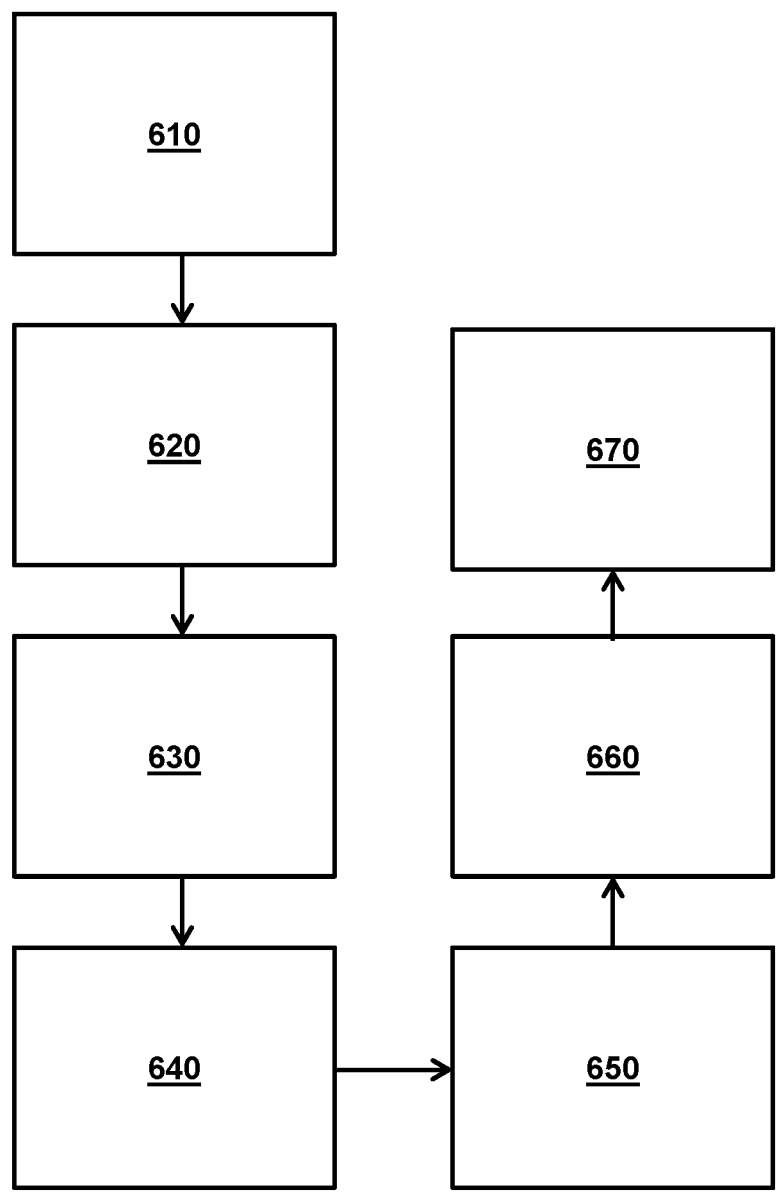
FIG. 6 is a simplified diagram illustrating an exemplary process of developing and deploying a predictive model to assess patient tissue in accordance with certain aspects of the present disclosure.

The exemplary process continues as shown in FIG. 6, where, at 640, one or more features are determined. In general, the development of the predictive model includes taking the available sensor data and determining the best combination of features (e.g., metrics for particular sensors) and a classifier to use to generate the tissue assessment. As previously mentioned, as used in the present disclosure, a "feature" is a quantity determined from one or more metrics—as calculated for one or more particular temperature sensor(s). For example, while "variance" is a metric, "Variance3" (i.e., the variance of the signal from Sensor 3) can be a feature. A feature can also be calculated from multiple metrics or from multiple sensors. For example, a feature may be the difference between Variance3 and Variance9 or could be the difference between Variance3 and Wavelet Entropy9.

Some exemplary features may utilize temperature data from one side of a body and temperature data from a corresponding location on the opposite side of the body, such as, a feature calculated as the difference between mirror-image sensors (i.e., at corresponding/mirrored locations on different patches). A non-exclusive list of feature examples follows (with references to the exemplary sensor numbers/positions indicated in the example of FIG. 1):

SideDiff: SideDiff is the difference between the mean of all left-side sensor means and the mean of all right-side sensor means (e.g., Mean of the means of Sensors 1 to 8—Mean of the means of Sensors 9 to 16).

UODiff: UODiff is the difference between the mean of all the Left Upper Outer quadrant sensor means and the mean of all the Right Upper Outer quadrant sensor means (e.g., Mean of the means of Sensors 2, 3, 4, 5, 7—Mean of the means of Sensors 10, 12, 13, 14, 15).

UIDiff: Miff is the difference between the mean of all the Left Upper Inner quadrant sensor means and the mean of all the Right Upper Inner quadrant sensor means (e.g., Mean of the means of Sensors 4, 5, 6—Mean of the means of Sensors 11, 12, 13).

LODiff: LODiff is the difference between the mean of all the Left Lower Outer quadrant sensor means and the mean of all the Right Lower Outer quadrant sensor means (e.g., Mean of the means of Sensors 1, 8—Mean of the means of Sensors 9, 16).

LIDiff: LIDiff is the difference between the mean of all the Left Lower Inner quadrant sensor means and the mean of all the Right Lower Inner quadrant sensor means (e.g., Mean of Sensor 1—Mean of Sensor 16).

Sensor1: Difference in mirror-image sensor means: Mean of Sensor 2–Mean of Sensor 15.

Sensor2: Difference in mirror-image sensor means: Mean of Sensor 3–Mean of Sensor 14.

Sensor3: Difference in mirror-image sensor means: Mean of Sensor 4–Mean of Sensor 13.

Sensor4: Difference in mirror-image sensor means: Mean of Sensor 5–Mean of Sensor 12.

Sensor5: Difference in mirror-image sensor means: Mean of Sensor 6–Mean of Sensor 11.

Sensor6: Difference in mirror-image sensor means: Mean of Sensor 7–Mean of Sensor 10.

Sensor7: Difference in mirror-image sensor means: Mean of Sensor 8–Mean of Sensor 9.

SensorDiff1: Difference in two of the Upper Outer Sensors' means: Mean of Sensor 14–Mean of Sensor 7.

SensorDiff2: Difference in the means of the means of a first sensor combination: Mean of: (the means of Sensors 14, 15, 16)–Mean of: (the means of Sensors 4, 7, 8).

SensorDiff3: Difference in the means of the means of a second sensor combination: Mean of: (the means of Sensors 9, 13)–Mean of: (the means of Sensors 5, 6).

SensorDiff4: Difference in two of the Central Sensors' means: Mean of Sensor 13–Mean of Sensor 5.

Feature subset selection 650 can include determining a subset of features most useful for tissue assessment and eliminating irrelevant ones from the dataset. Obtaining a smaller set of features and retaining the optimal salient characteristics of the temperature data not only decreases processing time but also leads to more compactness of the models learned, better generalization, and comprehensibility of the results. Two examples of feature subset selection techniques include: (i) Filter Methods, in which the selection of features is independent of the classifier used, and (ii) Wrapper Methods, in which the features are selected using the classifier.

Filter Methods can rely on general characteristics of the data to evaluate and to select the feature subsets. Filters can be used as a pre-processing step since they are simple and fast. One example of a filter method is to apply a univariate criterion separately on each feature. In some examples, a t-test was applied on each feature and the resulting p-value (or the absolute values of t-statistics) was compared for each feature as a measure of how effective it is at separating groups.

Wrapper Methods use a classifier to perform assessment using every possible feature subset and select the feature subset that gives the best assessment accuracy. This method can improve a classifier's performance since both learning a classifier and selecting features use the same bias. Since a classifier is built as many times as the number of feature subsets generated, such classifiers can be computationally expensive and should not be considered if such is a consideration.

Sequential feature selection is one wrapper technique. This method selects a subset of features by sequentially adding (forward search) or removing (backward search) features until certain stopping conditions are satisfied. Forward sequential feature selection in a wrapper fashion may be used to find important features. More specifically, since one of the goals can be to minimize assessment errors (AE), the feature selection procedure can perform a sequential search using the AE of a classifier on each candidate feature subset as the performance indicator for that subset. A training set is used to select the features and to fit the classifier, and the testing set is used to evaluate the performance of the finally selected feature subset. During the feature selection procedure, to evaluate and to compare the performance of each candidate feature subset, a stratified 10-fold cross-validation can be applied to the training set. In stratified ten-fold cross validation, the dataset can be split into ten approximately equally sized disjoint subsets. The subsets can be selected in a way that the proportion of benign to malignant samples is the same in all, e.g., stratified. In each fold or iteration, nine subsets can be used for ranking the features. The process can be repeated 10 times and the final feature subset selected. The above example is just one way in which a final feature subset can be selected and as such is not an essential feature of any implementation of the claimed subject matter.

Predictive Model Development and Evaluation 660 can involve developing a predictive model that can classify the input data into one of two types—presence of thermal anomaly/absence of thermal anomaly. A predictive model is a combination of selected features and classifiers and can be ranked based on the classification accuracy, sensitivity and specificity for the studied dataset. Classifier performance depends greatly on the characteristics of the data to be assessed. Because there may be no single classifier that works best on all given problems, several classifiers may be evaluated to understand which classifier performs most effectively.

In some embodiments, supervised learning may be preferred. In this type of learning, during the training phase, both the features (input) and the corresponding class label (pathology/output) are used to help the classifier learn the relationship between the input and output. After training, only the features of the test data are used. The classifier then automatically predicts the unknown class label with the help of the knowledge gained during the training phase. Classifiers can include, for example, Bayes Net (BN), Naive Bayes (NB), Radial Basis Function Neural Network (RBFNN), Support Vector Machine (SVM) with a Radial Basis Function kernel, Sequential Minimal Optimization (SMO), Naive Bayes Tree (NBTree), Decision Tree (DT), XGBoost, Adaboost and Bagging meta-classifiers. A few other classifiers like Back Propagation Neural Network (BPNN), Probabilistic Neural Network (PNN), Gaussian Mixture Model (GMM), and Fuzzy Equivalence (FEQ) may also be utilized.

In one implementation, the above-mentioned stratified ten-fold cross validation technique was employed to build and evaluate these classifiers, i.e., the dataset was split into 10 subsets. Nine subsets were used for training, and the remaining subset was used for testing to get performance measures like accuracy, sensitivity, and specificity. The process was repeated nine more times and the final performance measure was taken as the average of measures obtained in all ten iterations. Several combinations of feature subsets and classifiers could be evaluated as part of the feature selection step described earlier to select the best feature set-classifier combination (also known as the predictive model). For example, one implementation of a feature set-classifier combination determined to have a high accuracy of prediction includes: Mean11, Mean13, Cum2_12, Cum2_15, LLE9, LLE2, PE8, Cum2_11, LLE6, SHE1, SHE12, LLE7, and Mean1 in the SVM classifier with Radial Basis Function kernel.

Determination of the predictive model can be dependent on data acquisition time. In some implementations, the period of time can be approximately 24 hours. As used herein, term "approximately 24 hours" is intended to mean between 22 hours and 26 hours. In some implementations that have an approximately 24-hour acquisition time, the metric(s) used in the predictive model can include one or more of a Mean, a Largest Lyapunov Exponent, and a Short Hurst Exponent. In some implementations, the features can then include one or more of Mean1, LLE7, and SHE12. Also, the classifier can be an SVM classifier with a Radial Basis Function kernel. An extended feature set for use with the above classifier (or any other type of classifier) can include Mean11, Mean13, Cum2_12, Cum2_15, LLE9, LLE2, PE8, Cum2_11, LLE6, SHE1, SHE12, LLE7, and Mean1.

As used herein, when a term such as Mean1 is utilized, is intended to refer to the mean of the temperature data taken from a temperature sensor located at approximately the lower left center portion of the breast, as shown by the example of temperature sensor 1 in FIG. 1. Similarly, LLE7 refers to the Largest Lyapunov Exponent of the temperature data taken from a temperature sensor located at approximately the upper left corner of the breast, as shown by the example of temperature sensor 7 in FIG. 1. It should be understood that such locations are approximate and that the temperature data can be taken from the location shown, as well as any location generally proximate to it (e.g., within up to 22 mm. from the illustrated locations).

In other implementations, the acquisition time can be much shorter than 24 hours. For example the period of time of data acquisition can be approximately two hours (e.g., between 1 and 3 hours). In implementations that have an approximately two-hour acquisition time, the metric(s) used in the predictive model can include one or more of SensorDiff (e.g., any of the above SensorDiff features) and ApEn. In another implementation, the features can include one or more of SensorDiff3, ApEn3, and ApEn5. Also, the classifier can be an XGBoost classifier. An extended feature set for use with the above classifier (or any other type of classifier) can include SensorDiff1, ApEn3, ApEn5, LLE3, Var12, Cum2_12, SensorDiff2, SensorDiff4, LLE12, WEnt5, Mean5, WEnt7, LLE5, Mean7, SensorDiff3, LLE7, LLE15.

The previously discussed operations can be carried out on a historical dataset that has pathology information to train the classifier. This can be used to generate a trained predictive model that can assess whether new patient data exhibits any abnormality in the breast tissue. During Predictive Model Deployment 670, the predictive model can be used for new patient data assessment. A new dataset can be examined for the indication of any loose sensors or if the data collection was incomplete (by checking for the presence of out of range or zero values). If the data is usable, the features that were determined during the model development process can be calculated from the patient's temperature data. These features can then be input into the trained predictive model that will provide an assessment indicating the presence or absence of breast abnormalities.

Figure 7:
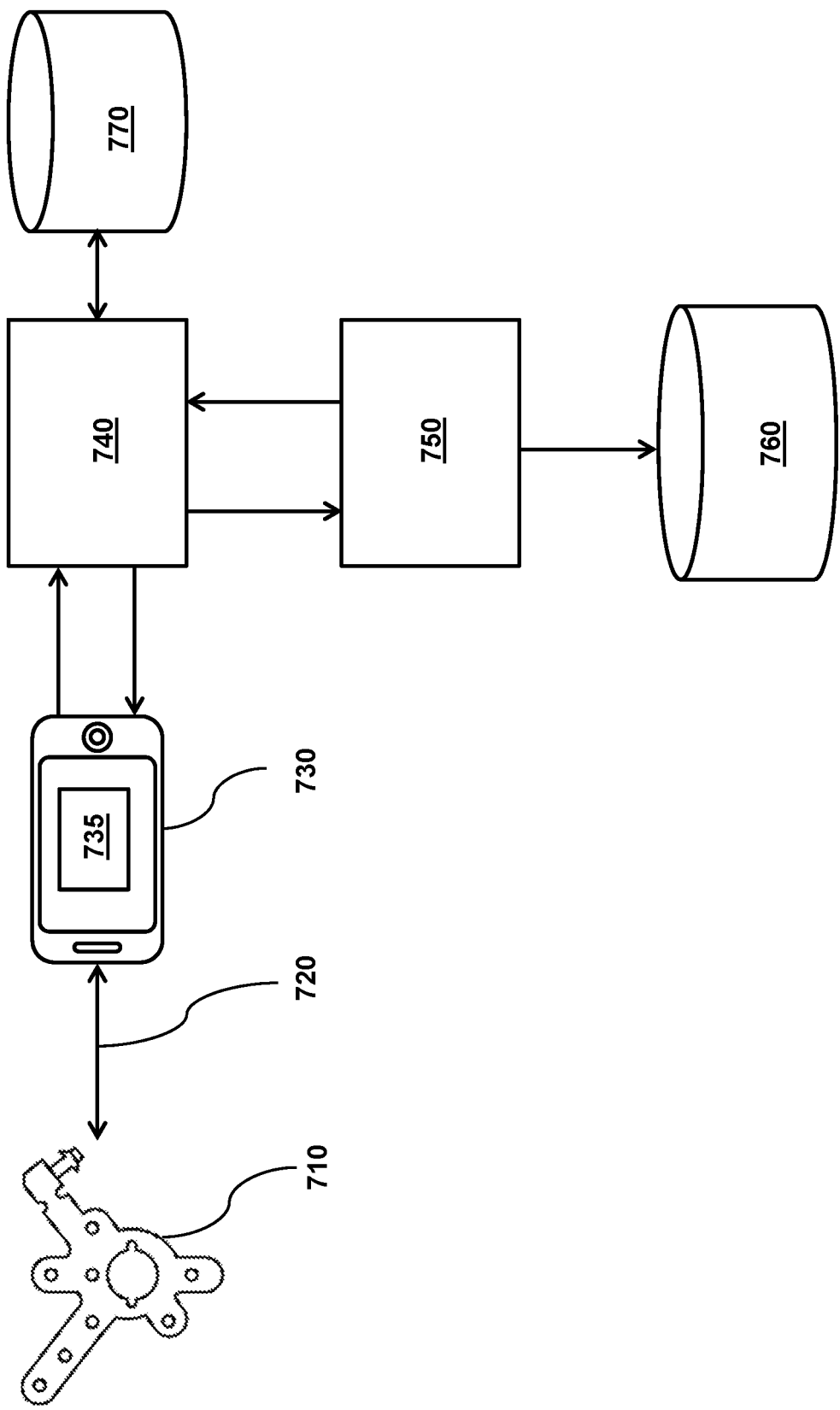
FIG. 7 is a simplified diagram illustrating an exemplary system for providing a tissue assessment in accordance with certain aspects of the present disclosure.

FIG. 7 illustrates one example of a system for capturing and analyzing temperature data to provide a tissue assessment. The system can include a wearable device 710, for example, as described herein, to capture and record temperature data. The wearable device may be in communication 720 (e.g., Bluetooth™ communication) with an application 735 on a computer or other device 730 (such as a smart phone belonging to the patient/user on which the application has been downloaded). The application 735 can also be in communication with local data manager 740 to manage the processing, analysis, and storage of the temperature data. Data manager 740 may be hosted in a cloud computing environment, on one or more remote servers, or on other computing devices in network communication with device 730. In some implementations, the cloud or servers may be local to a geographical region where the application 735 is used. Data manager 740 may receive temperature data from application 735 and may store the temperature data in a patient database 770 on the device and/or may send the temperature data to a core lab 750 for predictive analytics analysis. Core lab 750 can be, for example, one or more servers located at a central location that can receive and analyze temperature data from any number of deployed wearable devices. The core lab can utilize the data mining algorithms and predictive models described herein to analyze the temperature data and provide an assessment of the analyzed tissue.

The temperature data may also be anonymized prior to analysis at the core lab 750 to ensure user privacy. The anonymized temperature data and/or tissue assessments may be stored in the core lab database 760 for future reference and use. After the core lab 750 has analyzed the set of received temperature data, the results, which include an assessment of the measured tissue, may be sent back to data manager 740. From data manager 740, the assessment may be stored in a patient database 770 and/or displayed to the user via application 735.

The following is a description of an exemplary process which may be followed by a user in accordance with the system illustrated in FIG. 7. In the process, an application 735 is installed (optionally by the user) on a computing device 730, such as a smartphone or other smart device, and it can wirelessly communicate 720 with the recorder of the wearable device, in order to control the wearable device 710 and receive data collected by the temperature sensors on the wearable device 710. In some implementations, the application can include additional modules containing information to educate a user about breast disease or the use of the wearable device, data analysis modules, and options for ordering replacements and other parts of the wearable device.

When wireless device patches are properly contacted to the breasts, the user may initiate a connection, e.g., a Bluetooth™ connection, between the smart device and wearable device via the application. In some embodiments, the connection may occur automatically upon placement of the wearable device on the user. In other embodiments, a Bluetooth connection and the loaded application may be required for the connection between the wearable device and application to occur.

Once a connection 720 is established, the user may be notified through the application 735 about a test run. During the test run, the firmware can allow temperatures from the sensors to stabilize for a period of time, e.g., one minute, and subsequently check the sensor connections and temperature range. If the test run is successful, the user can initiate the scan in the application, and the application can send the appropriate command to the recorder to start the scan. Once a scan is initiated, a signal can be sent to the recorder to start collecting data and a timer can appear on the application counting backwards to zero illustrating to the user how much more time is required to complete the data collection process.

During the recording period, the user can proceed with normal daily activity. In certain embodiments, the data recording can continue even if the user moves away from, or out of range of device 730. Once the timer hits zero in application 735, connection 720 can be revalidated. If device 730 is still connected to wearable device 710, transfer of data from wearable device 710 to the application 735 can commence. If connectivity is not established, the user can be prompted to reestablish the connection between wearable device 710 and the computing device 730 to send the data.

Once the application at the computing device receives the temperature data, the temperature data may be transferred to a backend cloud environment, e.g., to a local database 770 for storage and optionally also to a centralized core lab 750 for analysis. Once the data is received and transmitted to the backend, an acknowledgement of the receipt of the data can be displayed on device 730. There may also be a message indicating that the result will be transmitted back to the user and/or their physician/insurance provider, when available.

At the core lab 750, the predictive model can analyze the data and obtain a tissue assessment indicating the presence or absence of any abnormality. Once the data collection process is complete and the temperature data has been transferred to the application successfully, the user may remove the patch and disconnect the data recorder.

Figure 8:
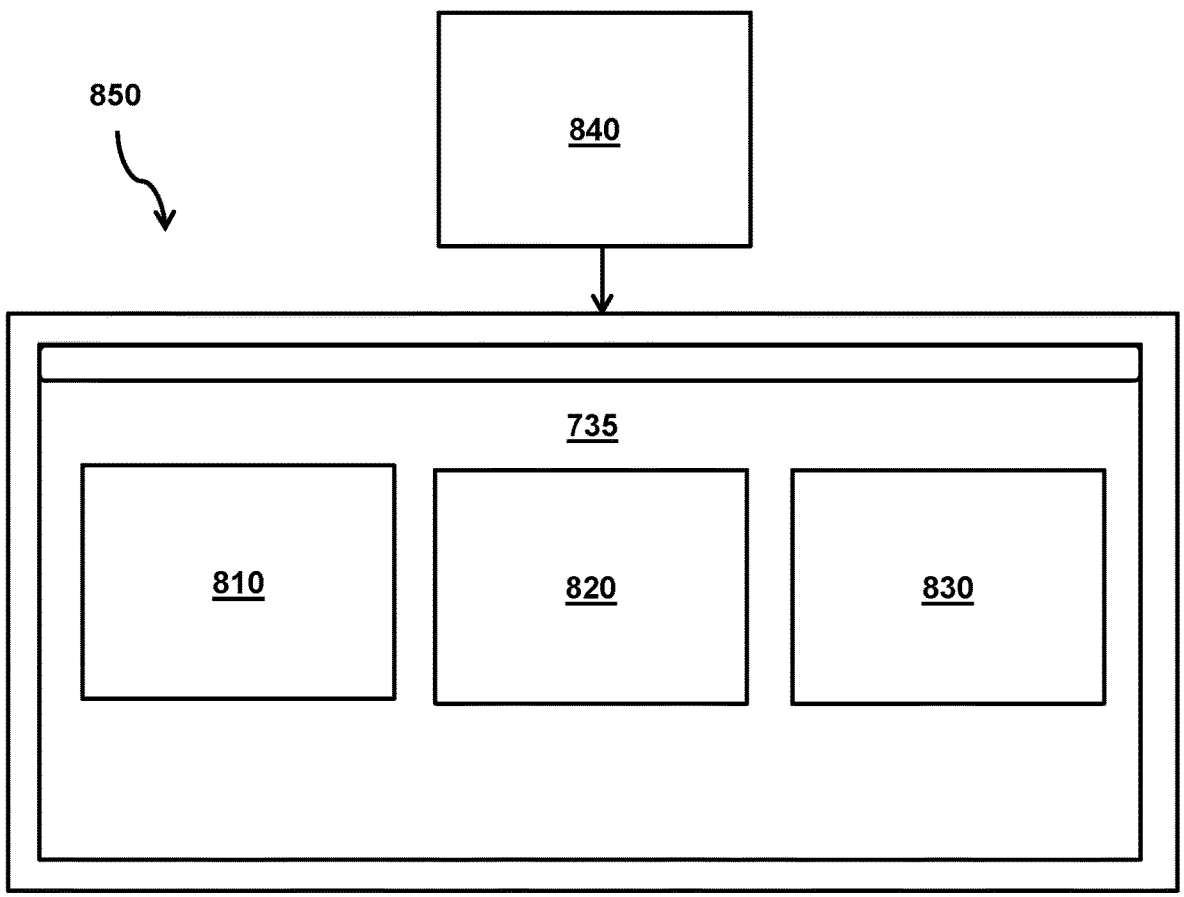
FIG. 8 illustrates a graphical user interface for reporting the outcome of the predictive model, in accordance with embodiments of the present invention.

As illustrated in FIG. 8, output 840 of the predictive model can be a tissue assessment that may be displayed to a user through a graphical user interface 850 of application 735. In some implementations, the output may indicate whether the results are normal 810, benign 820 or malignant 830. The assessment can optionally be electronically transmitted to a health care practitioner's computer system to allow gauging of overall breast wellness and to support further treatment decisions.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system for assessing tissue, the system comprising:
   a wearable device comprising patches being integrated with temperature sensors;
   at least one programmable processor; and
   a non-transitory, machine-readable medium storing instructions which, when executed by the at least one programmable processor, cause the at least one programmable processor to:
   receive temperature data captured by the temperature sensors integrated in patches in the wearable device worn by a human subject, the temperature sensors measuring surface temperatures at predetermined locations on two breasts of the human subject over a period of time;

calculate at least one metric of the temperature data, the at least one metric being indicative of changes of the temperature data over time;

calculate one or more features based on the at least one metric, at least one feature of the one or more features being calculated based on the temperature data representing the surface temperatures on both of the two breasts, wherein the at least one feature comprises at least one of a Largest Lyapunov Exponent (LLE) feature at a first location or a Short Hurst Exponent (SHE) feature at a second location; and input the one or more features to a classifier and determine, based on a result of the classifier, a tissue assessment indicative of a health condition of the two breasts of the human subject.

2. The system of claim 1, wherein the tissue assessment is one of normal, benign, or malignant, and wherein the at least one programmable processor is further configured to diagnose presence of early abnormal breast tissue changes based on the tissue assessment.

3. The system of claim 1, wherein the wearable device is a bra.

4. The system of claim 1, wherein the classifier is at least one of: Bayes Net (BN), Naive Bayes (NB), Radial Basis Function Neural Network (RBFNN), Support Vector Machine (SVM) with a Radial Basis Function kernel, Sequential Minimal Optimization (SMO), Naive Bayes Tree (NBTree), Decision Tree (DT), a gradient boost method of XGBoost, or Adaboost and Bagging meta-classifiers.

5. The system of claim 1, wherein the at least one metric of the temperature data includes Short Hurst Exponent (SHE) and Largest Lyapunov Exponent (LLE).

6. The system of claim 5, wherein the at least one metric further includes at least one of a SensorDiff or an ApEn.

7. The system of claim 6, wherein the at least one feature further includes at least one of a SensorDiff3, an ApEn3, or an ApEn5.

8. The system of claim 1, the operations further comprising analyzing the temperature data to identify and remove data outliers prior to calculating the at least one metric.

9. The system of claim 1, wherein to calculate one or more features based on the at least one metric, the at least one programmable processor is further configured to:
    determine the at least one metric of the temperature data captured by the temperature sensor associated with a location that is predetermined to be associated with breast cancer.

10. The system of claim 1, wherein the at least one feature utilizes first temperature data from a first side of a body and second temperature data from a corresponding location on an opposite side of the body.

11. The system of claim 1, wherein the period of time is twenty-four hours.

12. The system of claim 11, wherein the at least one metric includes a Mean, a Largest Lyapunov Exponent, and a Short Hurst Exponent.

13. The system of claim 12, wherein the at least one feature includes at least one of an LLE7, or an SHE12.

14. The system of claim 11, wherein the classifier is an SVM classifier with a Radial Basis Function kernel.

15. The system of claim 1, wherein the period of time is two hours.

* * * * *